United States Patent [19]

Ostrowski

[11] 4,307,262

[45] Dec. 22, 1981

[54] USE OF ZINC DIPHENYL AS ALKYLATION INHIBITOR IN LIGAND-COMPLEXING PROCESS

[75] Inventor: Paul C. Ostrowski, Webster, Tex.

[73] Assignee: Tenneco Chemicals, Inc., Saddle Brook, N.J.

[21] Appl. No.: 153,977

[22] Filed: May 28, 1980

[51] Int. Cl.³ .................. C07F 1/08; C07F 3/06; C07C 7/156

[52] U.S. Cl. .................. 585/848; 260/438.1; 585/864

[58] Field of Search .......... 260/429.9, 438.1; 585/864, 848

[56] References Cited

U.S. PATENT DOCUMENTS

| | | | |
|---|---|---|---|
| 3,651,159 | 3/1972 | Long et al. | 260/438.1 |
| 3,857,869 | 12/1974 | Turnbo | 260/438.1 |
| 3,868,398 | 2/1975 | Kroll et al. | 260/438.1 |
| 4,014,950 | 3/1977 | Keyworth et al. | 260/438.1 |
| 4,066,679 | 1/1978 | Long et al. | 585/848 |
| 4,091,045 | 5/1978 | Walker | 585/848 |

*Primary Examiner*—Winston A. Douglas
*Assistant Examiner*—Raymond K. Covington
*Attorney, Agent, or Firm*—Evelyn Berlow

[57] ABSTRACT

In processes in which liquid sorbents that are solutions in an aromatic hydrocarbon or halogenated aromatic hydrocarbon of a bimetallic salt complex having the generic formula $M_I M_{II} X_n$·Aromatic, wherein $M_I$ is Group I-B metal, $M_{II}$ is a Group III-A metal, X is halogen, n is the sum of the valences of $M_I$ and $M_{II}$, and Aromatic is a monocyclic aromatic hydrocarbon or halogenated aromatic hydrocarbon are used to separate complexible ligands from a gas feedstream that comprises an olefin having 2 or 3 carbon atoms, alkylation of the aromatic hydrocarbon or halogenated aromatic hydrocarbon is inhibited by incorporating in the liquid sorbent a small amount of zinc diphenyl.

10 Claims, No Drawings

USE OF ZINC DIPHENYL AS ALKYLATION INHIBITOR IN LIGAND-COMPLEXING PROCESS

This invention relates to an improved process for the separation of complexible ligands from gas feedstreams that utilizes complexing of the ligands with liquid sorbents that are solutions of bimetallic salt complexes having the generic formula $M_IM_{II}X_n$.Aromatic, wherein $M_I$ is a Group I-B metal, $M_{II}$ is a Group III-A metal, X is halogen, n is the sum of the valences of $M_I$ and $M_{II}$, and Aromatic is a monocyclic aromatic hydrocarbon or halogenated aromatic hydrocarbon having 6 to 12 carbon atoms. The improvement comprises the inclusion in the liquid sorbents of an amount of zinc diphenyl which when dissolved in the sorbents inhibits the alkylation of their aromatic component by the lower olefins that are present in the gas feedstream.

Bimetallic salt complexes that have the generic formula $M_IM_{II}X_n$.Aromatic are known to be useful in the separation from gas mixtures of such complexible ligands as olefins, aceytylenes, aromatics, and carbon monoxide. For example, in U.S. Pat. No. 3,651,159, Long et al. disclosed a process in which a sorbent solution of cuprous aluminum tetrahalide in toluene was used to separate ethylene, propylene, and other complexible ligands from a gas feedstream. The complexed ligands were recovered by ligand exchange with toluene. The resulting solution of cuprous aluminum tetrahalide.toluene in toluene was recycled and used to separate additional quantities of the complexible ligand from the gas feedstream. Walker et al. in U.S. Pat. No. 3,647,843 disclosed a process in which a hydrocarbon pyrolysis gas feedstream was contacted with a cuprous aluminum tetrachloride solution in toluene to separate acetylene from the gas feedstream as a solution of the complex $HC\equiv CH.CuAlCl_4$ in toluene. Acetylene was stripped from this complex, and the cuprous aluminum tetrachloride.toluene solution was recycled.

In processes such as those disclosed by Long et al. and by Walker et al. in which a liquid sorbent containing a bimetallic salt complex is recycled without purification and is used for long periods of time, there is a gradual increase in the amounts of reaction by-products and other impurities in it until sufficient impurities are present to interfere with the efficient operation of the process. For example, when the liquid sorbent is contacted with a gas stream that contains ethylene and/or propylene, some of the olefin reacts with the aromatic hydrocarbon or halogenated aromatic hydrocarbon in the sorbent to form alkylated aromatic compounds and some undergoes polymerization to form olefin oligomers. These reactions are catalyzed by hydrogen chloride or other acidic compounds that are in the gas feedstream or are formed as by-products of the reaction between the liquid sorbent and trace amounts of water or certain other impurities in the gas feedstream.

In ligand separation processes that involve complexing of ligands with a liquid sorbent that is a solution of a bimetallic salt complex in an aromatic hydrocarbon, it is necessary to minimize the formation of alkylated aromatic compounds because the presence of these compounds not only adversely affects the complexing ability of the liquid sorbent, but it also leads to corrosion of the processing equipment and copper metal deposition.

A number of procedures have been proposed in the prior art for inhibiting the reactions between the liquid sorbent and lower olefins to form alkylated aromatic compounds and olefin oligomers by removing or neutralizing the acidic materials that catalyze these reactions, but none has proven to be entirely satisfactory. Some of these procedures fail to reduce the amounts of reaction by-products to the desired very low levels, while others interfere with the efficient operation of the ligand separation process. For example, Long et al. in U.S. Pat. Nos. 3,651,195, 3,887,600, 4,066,679, and 4,141,960 disclosed the use of a small amount of a neutralizing agent, such as ammonia or an organic nitrogen compound, to reduce the residual catalytic activity or acidity of the system. They taught that the amount of neutralizing agent should be merely enough to react with the free acidity of the system because larger amounts of the neutralizing agent will cause precipitation of the copper salt from the solution and lead to the formation of different catalytic species. They preferred to use from 0.01 to 1 wt. percent, based on the liquid sorbent, of the neutralizing agent. Combinations of organic phosphines and organic nitrogen bases were used by Horowitz et al. in U.S. Pat. No. 3,758,609 to inhibit side reactions during olefin complexing processes in which liquid sorbents containing cuprous aluminum tetrachloride were used as the complexing agent. The useful organic nitrogen bases included substituted pyridines, tertiary alkyl amines, and tertiary alkyl aryl amines. Pyridine was said to be ineffective as an inhibitor because it reacts with the liquid sorbent to form precipitates that contain sizeable amounts of the organic base. In U.S. Pat. Nos. 3,755,487 and 3,758,608, soluble compounds of antimony, arsenic, and bismuth, phosphines, amines, and other additives are added to liquid sorbents that comprise cuprous aluminum tetrachloride to minimize side reactions, to reduce the corrosion effect of the cuprous salt solution, and to prevent the deposition of copper from the solution. Tyler et al. in U.S. Pat. Nos. 3,776,972 and 3,933,878 disclosed that trialkyl phosphines and other complexible ligands can be used to inhibit alkylation and polymerization side reactions in olefin-complexing processes employing liquid sorbents that comprise cuprous aluminum tetrachloride and an aromatic hydrocarbon.

In accordance with this invention, it has been found that the alkylation and other side reactions that take place when a gas feedstream that comprises ethylene and/or propylene is contacted with a liquid sorbent that comprises a bimetallic salt complex of the formula $M_I.M_{II}X_n$.Aromatic wherein $M_I$ is a Group I-B metal, $M_{II}$ is a Group III-A metal, X is halogen, n is the sum of the valences of $M_I$ and $M_{II}$, and Aromatic is a monocyclic aromatic hydrocarbon or halogenated aromatic hydrocarbon having 6 to 12 carbon atoms can be substantially reduced by incorporating in the liquid sorbent an inhibiting amount of zinc diphenyl. The presence of zinc diphenyl in the liquid sorbent makes it possible to reversibly absorb ethylene and/or propylene without encountering appreciable deterioration of the liquid sorbent resulting from reaction between the liquid sorbent and the olefins, thereby lengthening the time that the liquid sorbent can be used without purification in the ligand separation process.

The liquid sorbents that are stabilized by the process of this invention are solutions of a bimetallic salt complex in an aromatic hydrocarbon or a halogenated aromatic hydrocarbon. The bimetallic salt complexes have the generic formula $M_IM_{II}X_n$. Aromatic. $M_I$ is a Group I-B metal; that is, copper, silver, or gold. Copper (I) is the preferred metal. $M_{II}$ is Group III-A metal; that is boron, aluminum, gallium, indium, or thallium. Boron and aluminum are the preferred metals, aluminum being particularly preferred. X is halogen, i.e., fluorine, chlorine, bromine, or iodine; it is preferably chlorine or bromine. The sum of the valences of $M_I$ and $M_{II}$ is represented by n. Aromatic is a monocyclic aromatic hydrocarbon or halogenated aromatic hydrocarbon having 6 to 12 carbon atoms, and preferably 6 to 9 carbon atoms, such as benzene, toluene, ethylbenzene, xylene, mesitylene, chlorobenzene, bromobenzene, iodobenzene, dichlorobenzene, dibromobenzene, chlorotoluene, bromotoluene, iodotoluene, or chloroxylene. It is preferably benzene or toluene. Illustrative of these bimetallic salt complexes are the following: $CuBF_4$.benzene, $CuBCl_4$.benzene, $AgBF_4$.mesitylene, $AgBCl_4$.xylene, $AgAlCl_4$.xylene, $AgAlBr_4$.bromobenzene, $CuGaCl_4$.toluene, $CuInI_4$.1,2-dichlorobenzene, $CuTlI_4$.p-chlorotoluene, and the like. The preferred bimetallic salt complexes are $CuAlCl_4$.benzene, $CuAlCl_4$.toluene, and $CuAlBr_4$.benzene. The aromatic hydrocarbon or halogenated aromatic hydrocarbon in which the bimetallic salt complex is dissolved is usually and preferably the same as that used in the preparation of the bimetallic salt complex, but if desired it may be a different one. The total amount of aromatic hydrocarbon or halogenated aromatic hydrocarbon in the liquid sorbent, that is, the amount in the bimetallic salt complex plus the amount used as solvent, is at least 10 mole percent of the amount of the bimetallic salt $M_I M_{II} X_n$ that is present. It is preferred that the amount of aromatic hydrocarbon or halogenated aromatic hydrocarbon be 100 to 450 mole percent of the amount of the bimetallic salt. The particularly preferred liquid sorbents contain 25 to 75 percent by weight of $CuAlCl_4$. benzene in benzene or $CuAlCl_4$.toluene in toluene.

In the practice of this invention, a gas feedstream that contains ethylene, propylene, or a mixture thereof is contacted with a liquid sorbent that contains an alkylation-inhibiting amount of zinc diphenyl. When the gas feedstream is contacted with the inhibitor-containing sorbent, any water that is in the gas feedstream reacts with the zinc diphenyl to form zinc oxide and benzene, as is shown in the following equation:

$$Zn(C_6H_5)_2 + H_2O \rightarrow ZnO + 2C_6H_6 \quad (1)$$

rather than with the cuprous aluminum tetrachloride in the liquid sorbent by the reactions shown in the following equations:

$$2CuAlCl_4.\text{toluene} + H_2O \rightarrow HCl + CuCl + CuAlCl_4.Al(OH)Cl_2.\text{toluene} \quad (2)$$

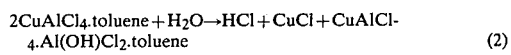
$$CuAlCl_4.Al(OH)Cl_2.\text{toluene} \rightarrow HCl + CuAlCl_4.AlOCl.\text{toluene} \quad (3)$$

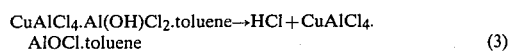

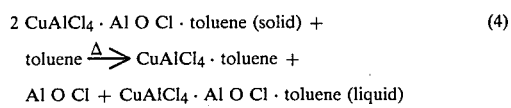

which yield as a reaction by-product hydrogen chloride, which catalyzes alkylation and other side reactions.

The amount of zinc diphenyl that is incorporated in the liquid sorbent is at least the amount that is required to remove from the gas feedstream the traces of water and other impurities that yield hydrogen chloride and other acidic compounds when they react with the bimetallic salt complex in the sorbent. In most cases, from 0.1 mole percent to 20 mole percent, based on the copper or other Group I-B metal in the bimetallic salt complex, of zinc diphenyl is used. Preferably, from 1 mole percent to 10 mole percent of the inhibitor is used to inhibit the side reactions.

While all of the zinc diphenyl may be added to the liquid sorbent before the sorbent is contacted with the gas feedstream, it is preferred that a minor portion (less than 50%) of the inhibitor be present at the start of the ligand-separation process and that the remainder be added continuously or intermittently during the ligand-separation process at approximately the rate at which zinc diphenyl is being removed from the liquid sorbent by reaction with water or other impurities in the gas feedstream.

Either zinc diphenyl or a solution of zinc diphenyl in a liquid aromatic hydrocarbon or halogenated aromatic hydrocarbon may be added to the liquid sorbent. The zinc diphenyl is preferably added as a saturated solution in benzene or toluene.

The zinc diphenyl that is used to stabilize the liquid sorbent by inhibiting alkylation of the aromatic compounds in it may be prepared by any suitable and convenient procedure. For example, it can be prepared by the Grignard reaction from zinc chloride and phenyl magnesium bromide. After separation from the reaction mixture and vacuum distillation to remove etherates of zinc diphenyl and other volatile reaction byproducts, the product is preferably dissolved in toluene to form a saturated 0.46 M solution of zinc diphenyl in toluene. Because zinc diphenyl reacts with oxygen, air must be excluded from the compound, from zinc diphenyl solutions, and from liquid sorbents that contain zinc diphenyl.

This procedure for the stabilization of liquid sorbents by inhibiting alkylation of the aromatic compounds in the sorbent is useful not only in processes in which ethylene and/or propylene is being separated from gas feedstreams but also in those in which carbon monoxide or another complexible ligand is being separated from a gas feedstream that contains trace amounts of the lower olefins as impurities.

The invention is further illustrated by the following examples.

EXAMPLE 1

A. A liquid sorbent that contained 28.6 mole percent of cuprous aluminum tetrachloride and 71.4 mole percent of toluene was prepared by adding 1.1 moles of cuprous chloride to 1 mole of anhydrous aluminum chloride in toluene. The resulting solution was filtered to remove unreacted cuprous chloride and insoluble impurities from it.

B. To the liquid sorbent was added a sufficient amount of a saturated solution of zinc diphenyl in toluene to form a solution that contained 7.36 mole percent of zinc based on copper in the liquid sorbent.

C. The zinc diphenyl-containing liquid sorbent was contacted with propylene at 65° C. at a pressure of 450 torr for 67 hours. The resulting liquid sorbent that contained the propylene-cuprous aluminum tetrachloride complex was fed to a stripping column in which it was brought into contact with benzene vapor at 95° C. The mixture of benzene vapor and olefins that left the column was cooled to separate the benzene from the olefins. The stripped liquid sorbent was analyzed to determine the amount of alkylation that had taken place. The results obtained are summarized in Table I.

From the data in Table I, it will be seen that during the process in which propylene was contacted with a liquid sorbent that comprised cuprous aluminum tetrachloride and toluene for 67 hours, the alkylation of toluene was substantially prevented by the addition of a small amount of zinc diphenyl to the liquid sorbent.

Comparative Example A

The procedure described in Example 1 was repeated except that zinc diphenyl was not added to the liquid sorbent before the sorbent was contacted with propylene and that the sorbent was contacted with propylene for only 0.5 hour. After the complexed propylene had been removed from it, the stripped liquid was analyzed to determine the amount of alkylation that had taken place. The results obtained are summarized in Table I.

From the data in this table, it will be seen that the toluene in the uninhibited liquid sorbent underwent considerable alkylation when the liquid sorbent was contacted with propylene.

TABLE I

| Analysis of Inhibited and Uninhibited Liquid Sorbent After Contact With Propylene at 65° C. at 450 Torr | | |
| --- | --- | --- |
| | Liquid Sorbent containing 7.36 mole percent of Zinc Diphenyl | Uninhibited Liquid Sorbent |
| Time of Contact with Propylene (Hours) | 67 | 0.5 |
| Analysis (mmol) | | |
| Monoisopropyltoluene | 0.095 | 23.40 |
| Diisopropyltoluene | <0.001 | 7.15 |
| Triisopropyltoluene | <0.001 | 0.038 |
| Total isopropyl groups | 0.095 | 37.81 |
| Copper (total) | 20.3 | 31.0 |
| Copper metal | 0.301 | — |
| Ratio — $\frac{isopropyl}{copper}$ | 0.0047 | 1.220 |

EXAMPLE 2

To a liquid sorbent prepared by the procedure of Example 1A that contained 6.760 parts by weight (16.3 mmol) of cuprous aluminum tetrachloride and 32.2 mmol of toluene was added 0.469 part by weight (2.14 mmol) of zinc diphenyl under nitrogen. After the liquid sorbent had been heated to 55° C., 8.64 mmol of propylene was added to it. After 19.1 hours at 55° C., the reaction mixture was vacuum stripped twice to yield 7.68 mmol of gas that contained 7.43 mmol of propylene and 0.069 mmol of propane.

EXAMPLE 3

To a liquid sorbent prepared by the procedure of Example 1A that contained 6.760 parts by weight (16.3 mmol) of cuprous aluminum tetrachloride and 32.2 mmol of toluene was added 0.469 part by weight (2.14 mmol) of zinc diphenyl under nitrogen. After the sorbent had been heated to 84° C., 7.70 mmol of propylene was added to it. The reaction mixture was heated to 84° C. for 23 hours and then vacuum stripped twice to yield a gas that contained 6.83 mmol of propylene, 0.002 mmol of hexenes, 0.022 mmol of benzene, and 0.547 mmol of toleune.

EXAMPLE 4

A. To a 5 ml. portion of a liquid sorbent prepared by the procedure of Example 1A that contained 14.4 mmol of cuprous aluminum tetrachloride and 34 mmol of toluene was added 1 ml. of a saturated zinc diphenyl solution in toluene (0.46 mmol zinc diphenyl and 9.2 mmol toluene). The liquid sorbent was heated to 80° C. and 4.41 mmol of ethylene was added to it. After 17 hours at 80° C., the reaction mixture was stripped under vacuum. The recovered gas contained 99.9% of the ethylene that had been added to the liquid sorbent.

B. To the liquid sorbent from which ethylene had been recovered in Example 4A was added 28 mmol of toluene. The resulting liquid sorbent was heated to 84° C. and 3.07 mmol of propylene was added to it. After 17 hours at 84° C., the reaction mixture was stripped under vacuum and then cooled to 25° C. An additional 6.56 mmol of propylene was added to the liquid sorbent. After 2.5 hours at 25° C., the reaction mixture was stripped under vacuum. The gas that was recovered contained 94.8% of the propylene that had been added to the liquid sorbent.

EXAMPLE 5

When the procedure described in Example 4 was repeated except that a saturated solution of zinc diphenyl in benzene was added to a liquid sorbent that was a solution of cuprous aluminum tetrachloride in benzene, similar results were obtained.

EXAMPLE 6

A. To a 5 ml. portion of a liquid sorbent prepared by the procedure of Example 1A that contained 13.8 mmol of cuprous aluminum tetrachloride was added 3 ml. of a saturated zinc diphenyl solution in toluene to form a liquid sorbent that contained 1.26 mmol of zinc diphenyl (9.1 mole % of zinc diphenyl based on the copper in the liquid sorbent). The liquid sorbent was heated to 80° C., and 2.66 mmol of propylene was added to it. After 17 hours at 80° C., the reaction mixture was stripped under vacuum. The gas that was recovered contained 95.8% propylene, 3.6% propane and 0.6% ethane. The residual liquid sorbent was found to contain 0.326 mmol of benzene, 25.1 mmol of toluene, and 0.015 mmol of isopropyltoluenes.

B. The residual liquid sorbent was mixed with 3 ml. of fresh toluene, complexed with 2.85 mmol of propylene at 80° C. for 19 hours, and then vacuum stripped. The gas that was recovered contained 96.2% of propylene, 3.3% of propane, and 0.3% of ethane. The second residual liquid sorbent contained 22.7 mmol of toluene, 0.065 mmol of benzene, and 0.013 mmol of isopropyltoluenes.

C. The second residual liquid sorbent was mixed with 3 ml. of fresh toluene, complexed with 3.31 mmol of propylene at 80° C. for 17 hours, and then vacuum stripped. The gas that was recovered contained 96.7% of propylene, 3.1% of propane, and 0.2% of ethane. The third residual liquid sorbent contained 22.5 mmol of toluene, 0.189 mmol of benzene, and 0.013 mmol of isopropyltoluenes.

D. The third residual liquid sorbent was mixed with 3 ml. of fresh toluene, complexed with 3.43 mmol of propylene at 80° C. for 16.7 hours, and then vacuum stripped. The gas that was recovered contained 96.4% of propylene, 3.3% of propane and 0.2% of ethane. The fourth residual liquid sorbent contained 20.2 mmol of toluene, 0.16 mmol of benzene, and 0.038 mmol of isopropyltoluenes.

During this 4-cycle process, 85% of all of the propylene added to the zinc diphenyl-containing liquid sorbent was recovered in the gas that was stripped from the liquid sorbent containing the propylene-cuprous aluminum tetrachloride complex. At the same time, about 30% of the zinc diphenyl reacted with water that was in the propylene added to the liquid sorbent to form zinc oxide and benzene.

What is claimed is:

1. In the process for the separation of complexible ligands from a gas feedstream that comprises ethylene, propylene, or mixtures thereof wherein (a) said gas feedstream is contacted with a liquid sorbent that is a solution in an aromatic hydrocarbon or halogenated aromatic hydrocarbon of a bimetallic salt complex having the formula $M_I M_{II} X_n$.Aromatic, wherein $M_I$ is a Group I-B metal, $M_{II}$ is a Group III-A metal, X is halogen, n is the sum of the valences of $M_I$ and $M_{II}$, and Aromatic is a monocyclic aromatic hydrocarbon or halogenated aromatic hydrocarbon having 6 to 12 carbon atoms, thereby forming a reaction mixture that comprises a solution of a complex of the complexible ligand and the bimetallic salt complex in the liquid sorbent, (b) the reaction mixture is separated from the gas feedstream, (c) the ligand is separated from the liquid sorbent in the reaction mixture, and (d) the liquid sorbent is recycled to Step (a), the improvement that comprises incorporating in said liquid sorbent from 0.1 mole percent to 20 mole percent, based on Group I-B metal in the bimetallic salt complex component of the liquid sorbent, of zinc diphenyl, thereby substantially reducing alkylation and other side-reactions and stabilizing said liquid sorbent.

2. The process of claim 1 wherein the liquid sorbent is a solution in an aromatic hydrocarbon or halogenated aromatic hydrocarbon of the bimetallic salt complex having the formula $CuAlCl_4$.Aromatic.

3. The process of claim 2 wherein the liquid sorbent is a solution of $CuAlCl_4$.toluene in toluene.

4. The process of claim 2 wherein the liquid sorbent is a solution of $CuAlCl_4$.benzene in benzene.

5. The process of claim 2 wherein from 1 mole percent to 10 mole percent, based on the copper in the bimetallic salt complex component of the liquid sorbent, of zinc diphenyl is incorporated in the liquid sorbent.

6. The process of claim 1 wherein less than 50% of the zinc diphenyl is present at the start of the ligand separation process and the remainder is added continuously during the ligand separation process.

7. The process of claim 1 wherein less than 50% of the zinc diphenyl is present at the start of the ligand separation process and the remainder is added intermittently during the ligand separation process.

8. The process of claim 1 wherein a solution of zinc diphenyl in a liquid aromatic hydrocarbon or halogenated aromatic hydrocarbon is added to the liquid sorbent.

9. The process of claim 1 wherein a saturated solution of zinc diphenyl in toluene is added to the liquid sorbent.

10. The process of claim 1 wherein a saturated solution of zinc diphenyl in benzene is added to the liquid sorbent.

* * * * *